(12) United States Patent
Bellenger et al.

(10) Patent No.: US 9,217,085 B2
(45) Date of Patent: Dec. 22, 2015

(54) METHOD OF COATING AN INORGANIC SUBSTRATE WITH A STABLE ORGANIC LAYER

(75) Inventors: Fabien Bellenger, Shanghai (CN); Floryan De Campo, Shanghai (CN); Camille Jourde, Paris (FR); Tao Zhang, Shanghai (CN)

(73) Assignee: SOLVAY (CHINA) CO;. LTD, Shanghai (CN)

( * ) Notice: Subject to any disclaimer, the term of this patent is extended or adjusted under 35 U.S.C. 154(b) by 0 days.

(21) Appl. No.: 13/811,526

(22) PCT Filed: Jul. 21, 2010

(86) PCT No.: PCT/CN2010/075361
§ 371 (c)(1),
(2), (4) Date: Jan. 22, 2013

(87) PCT Pub. No.: WO2012/009852
PCT Pub. Date: Jan. 26, 2012

(65) Prior Publication Data
US 2013/0122213 A1    May 16, 2013

(51) Int. Cl.
| | | |
|---|---|---|
| C08F 2/48 | (2006.01) |
| C09D 4/00 | (2006.01) |
| C03C 17/32 | (2006.01) |
| C07F 9/38 | (2006.01) |
| C07F 9/48 | (2006.01) |

(52) U.S. Cl.
CPC ............... *C09D 4/00* (2013.01); *C03C 17/324* (2013.01); *C07F 9/3826* (2013.01); *C07F 9/48* (2013.01)

(58) Field of Classification Search
CPC ........ C03C 17/324; C03C 17/28; C09D 4/00; C07F 9/3826; C07F 9/48
USPC ........................................... 427/508
See application file for complete search history.

(56) References Cited

U.S. PATENT DOCUMENTS

| | | | |
|---|---|---|---|
| 3,695,925 A * | 10/1972 | Weil .............................. 442/128 |
| 4,170,609 A | 10/1979 | Turner | |
| 4,605,779 A | 8/1986 | Matsuda et al. | |
| 7,420,081 B2 | 9/2008 | Dabdoub | |
| 7,442,831 B2 | 10/2008 | Dabdoub | |
| 2004/0253181 A1 | 12/2004 | Port et al. | |

(Continued)

FOREIGN PATENT DOCUMENTS

| | | |
|---|---|---|
| EP | 1 997 839 A1 | 12/2008 |
| WO | 2004/058275 A2 | 7/2004 |

(Continued)

OTHER PUBLICATIONS

International Search Report and Written Opinion of the International Searching Authority issued on Apr. 28, 2011, by the Chinese Patent Office as the International Searching Authority in International Patent Application No. PCT/CN2010/075361Authority.

(Continued)

*Primary Examiner* — Robert S Walters, Jr.
(74) *Attorney, Agent, or Firm* — Dentons US LLP

(57) ABSTRACT

A method for coating a metallic or inorganic substrate is described, such as metal or glass supports, with an organic layer comprising conjugated diene phosphinate or phosphonate compounds.

15 Claims, 4 Drawing Sheets

(56) References Cited

U.S. PATENT DOCUMENTS

2009/0269606 A1    10/2009  Matsumoto
2012/0202957 A1*    8/2012  Liu et al. ................ 526/275

FOREIGN PATENT DOCUMENTS

WO    2008/017721 A2    2/2008
WO    2011/050533 A1    5/2011

OTHER PUBLICATIONS

Extended European Search Report dated Oct. 5, 2015, issued in corresponding European Patent Application No. 10854882.7, 6 pages.

* cited by examiner

METHOD OF COATING AN INORGANIC SUBSTRATE WITH A STABLE ORGANIC LAYER

CROSS-REFERENCE TO PRIOR APPLICATIONS

This application is a National Stage of PCT/CN2010/075361, filed Jul. 21, 2010, and designating the United States (published in English on Jan. 26, 2012, as WO 2012/009852 A1), which is hereby expressly incorporated by reference in its entirety and assigned to the assignee hereof.

FIELD OF THE INVENTION

The present invention relates to a method for coating a metallic or inorganic substrate, such as metal or glass supports, with an organic layer.

BACKGROUND OF THE INVENTION

Processed allowing to provide the surface of metallic or glass substrates with various coatings are known, said coatings being e.g. useful for protecting metallic substrate from corrosion or for modifying surface properties of supports, for example for adjusting the wettability of a substrate (especially for enhancing the paintability).

In this connection a recurrent problem is the durability of the deposited coating.

Especially, phosphonic acids have been proposed for modifying surfaces, for example according to the method described in WO 2008/017721. In this connection, interesting coating layers based on gem-bisphosphonic compounds have been described as able to adsorb relatively strongly at surfaces and to form self assembled monolayers (SAMs). However, the durability of such layer is still limited by the interaction of the phosphonic group with the surface, which depends on the nature of the treated surface. Besides, the interactions are often not stable and may be reversed by hydrolysis under acidic or basic conditions or by washing with appropriate solvents. In many case, the stability of the interaction reveals unsufficient for ensuring an effective durability, especially on metals and inorganic surfaces such as glass.

DESCRIPTION OF THE INVENTION

One aim of the present invention is to provide a generic method allowing to provide a coating on any metallic or inorganic substrate, with a very good durability of the coating, and which especially allows an improved stability of the coating in comparison to the method disclosed in WO 2008/017721.

To this end, the present invention provides a new method of coating at least one surface of an inorganic substrate, which comprises the following steps:
(a) treating the at least one surface of the substrate by contacting said surface with compounds having the following formula (I):

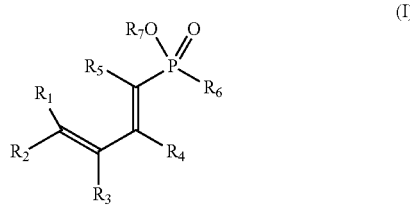

wherein:
each of $R_1$, $R_2$, $R_3$, $R_4$ and $R_5$, which are identical or different, represents hydrogen, or a alkyl, aryl, alkaryl, aralkyl, cycloalkyl, heterocycloalkyl or alkenyl group;

$R_6$ represents H, or a alkyl, aryl, alkaryl, aralkyl, cycloalkyl, heterocycloalkyl, or alkenyl group; or $R_6$ represents a —$OR_8$ group, wherein $R_8$ represents hydrogen or an alkyl, aryl, alkaryl, aralkyl, cycloalkyl, heterocycloalkyl, alkenyl group, or metals selected from the group consisting of Na, Li, Ca or ammonium compounds, $R_7$ represents hydrogen, alkyl, aryl, alkaryl, aralkyl, cycloalkyl, alkenyl groups, or a metal element selected from the group consisting of Na, Li, Ca or ammonium compounds, whereby the compounds of formula (I) adsorb on said surface; and (b) submitting the surface of the substrate modified in the treatment of step (a) to heat or UV irradiation, whereby the compounds of formula (I) react and form a stable coating on said surface.

In the scope of the instant invention, the inventors have now found that the succession of the above steps (a) and (b) allows providing a stable coating of inorganic surfaces, which exhibits an especially good durability. The process is especially suitable for modifying surfaces comprising, and preferably consisting of at least one metal and surfaces comprising, and preferably consisting of at least one metal oxide or silica, for example on surfaces comprising and preferably consisting of glass.

In step (a), the compounds of formula (I) adsorb on the surface of the substrate by the way of relatively strong interactions between the surface and the phosphonate or phosphinate head of the compounds (I), with interactions of the type disclosed in WO 2008/017721. These interactions are especially strong when the treated surface comprises at least one metal or glass.

Now, in the scope of the instant invention, the inventors have now surprisingly found that the obtained modified surface structure may then be fixed, in a very easy way, simply by submitting the modified surface to conditions allowing intermolecular reaction between the unsaturated group of compounds (I), which is simply obtained by submitting the surface to heat or UV irradiation, eventually in the presence of free radicals. It is thought that, in most cases, the reaction induces an inter-reticulation of compounds (I) on the surface of the substrate, and in some cases a polymerization, which crosslinks the structure obtained in step (a). In any case, an intermolecular reaction occurs allowing the formed layer to have an improved durability.

Such a possibility is especially unexpected since the reaction between a surface and compounds of the type of compounds (I) are known as very reversible. Because of this reversibility, it was unexpected that the compounds of formula (I) specifically interact on the modified surface and do not form polymers at the outside of the surface to be treated.

Advantageously, it reveals that the treatment of step (a) generally leads to the formation of self-assembled monolayers (SAMs) on the surface of the substrate, and said structure is in many case preserved after the reaction step (b), whereby the coating has the form of a stabilized SAM.

The coating obtained by making use of above steps (a) and (b) may be especially used for modifying the surface properties of the inorganic substrate, including for modifying its wettability, for example for adjusting its wettability which may especially be used in the field of paints, wherein step (a) and (b) may be used for applying a "primer" which enhances the paintability of a substrate intended to be painted.

The coating obtained in the scope of the process of the invention may furthermore be used as a first coating which may be post fonctionnalized or coated by one or more additional coating.

In these applications, the process of the invention reveals very advantageous since it allows obtaining a high stability of the "primer". Besides, since it generally leads to SAMs, it

Figure 1:
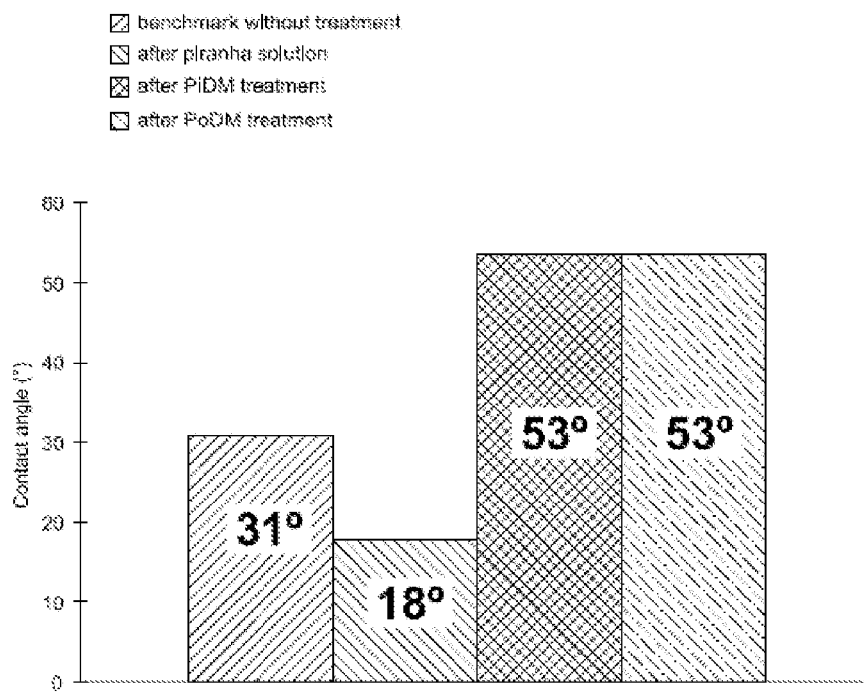
FIG. 1 shows the contact angle of the glass coupons of example 3.

Specific features and preferable embodiments of the invention will now be described in more details.

In the compounds of formula (I) used in the present invention, the alkyl and alkenyl group preferably comprise from 1 to 24 carbon atoms, said aryl comprises from 6 to 24 carbon atoms, and the alkaryl and aralkyl group preferably comprise from 7 to 24 carbon atoms. The cycloalkyl, heterocycloalkyl advantageously comprise from 3 to 24 carbon atoms.

In a preferred embodiment, the said alkyl and alkenyl comprise from 1 to 18 carbon atoms, the said aryl comprises from 6 to 18 carbon atoms, said alkaryl, aralkyl comprise from 7 to 18 carbon atoms, and said cycloalkyl, heterocycloalkyl comprise from 3 to 18 carbon atoms.

Preferably, $R_1$ and/or $R_2$ represent hydrogen, so the monomers so obtained are more reactive toward polymerization.

Preferably, $R_1$, $R_2$ and $R_4$, represent hydrogen; or preferably, $R_3$ and $R_5$ represent methyl. More preferably, $R_1$, $R_2$, and $R_4$ represent hydrogen and $R_3$, $R_5$ represent methyl.

In a specific embodiment of the present invention, when $R_6$ is not a —$OR_8$ group, compounds of formula (I) are conjugated diene phosphinate compounds.

In a preferred embodiment, any two or more of the group $R_1$, $R_2$, $R_3$, $R_4$, $R_5$, $R_6$, and $R_7$ are together formed into a cycloalkyl, or heterocycloalkyl group, which is preferably selected from 3 to 8 membered rings.

In another specific embodiment of the present invention, when $R_6$ is a —$OR_8$ group, compounds of formula (I) are conjugated diene phosphonate compounds.

In a preferred embodiment, any two of $R_1$, $R_2$, $R_3$, $R_4$ and $R_5$ are together formed into a cycloalkyl, or heterocycloalkyl group, which is preferably selected from 5, 6, 7 and 8 membered rings.

In a most preferred embodiment, when $R_6$ is a —$OR_8$ group, $R_6$ and $R_7$ are together formed into a cycloalkyl, or heterocycloalkyl group, which is preferably selected from 5, 6, 7 and 8 membered rings.

In another embodiment of the present invention, $R_6$ represents hydrogen or a OH group.

In another embodiment of the present invention, $R_7$ represents hydrogen.

In a preferred embodiment, $R_1$, $R_2$ and $R_4$ represent hydrogen, $R_3$ and $R_5$ represents methyl, $R_6$ represents hydrogen or a OH group and $R_7$ represents hydrogen.

Unless otherwise defined herein or below in the remainder of the specification, "Compounds of the present invention" or "compounds prepared according to the present invention" refers to compounds encompassed by the various description and structural formula disclosed herein. The compounds may be identified by either their chemical structure and/or chemical name.

The compounds of the present invention may contain one or more chiral centers and/or double bonds and therefore may exist as stereoisomers, such as Z- and E- or cis- and trans-isomers from cyclic structures or double bonds (i.e., geometric isomers), rotamers, enantiomers or diastereomers. Accordingly, when stereochemistry at chiral centers is not specified, the chemical structures depicted herein encompass all possible configurations at those chiral centers including the stereoisomerically pure form (e.g. geometrical isomerically pure, enantiomerically pure or diastereomerically pure) and enantiomeric and stereoisomeric mixtures, with the exception that when only one enantiomer is specified, the structure includes the other enantiomer as well. For example, in the event that a compound of formula I disclosed in the present invention is Z-form or trans-form for the double bonds close to P, one skilled in this art should understand that the E-form or cis-form of the compound is also disclosed. Enantiomeric and stereoisomeric mixtures can be resolved into their component enantiomers or stereoisomers using separation techniques or chiral synthesis techniques well known to those skilled in this art.

The compound of formula (I) can be obtained by different methods.

In an embodiment of the present invention, the method for preparing the compound of formula (I) comprises reacting an α,β- or β,γ-unsaturated ketone or aldehyde with a phosphinic or phosphorous acid or its derivatives.

When compounds of formula (I) are conjugated diene phosphonate compounds, the method comprises the step of: reacting α,β- or β,γ-unsaturated ketones or aldehydes having the formula II or III,

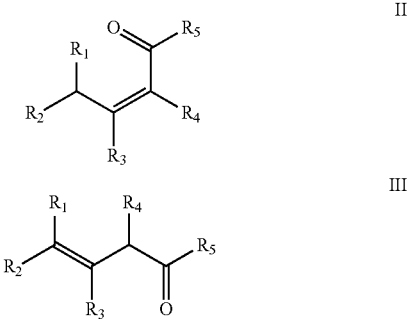

With a phosphorous acid or its derivatives having the structure,

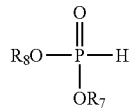

To obtain a conjugated diene phosphonate compound having the formula IV,

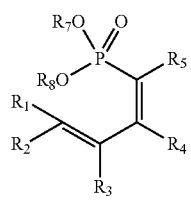

IV

According to the method of the present invention, said compound II or III is added in the molar ratio of (1~1.5):1 relative to said phosphorous acid or its derivatives; or preferably (1~1.2):1 relative to said phosphorous acid or its derivatives. The reaction time remains 4~24 hours, or preferably 4-8 hours. The reaction temperature remains at 0~100° C., or preferably 20~60° C.

One potential mechanism to explain the selectivity of the reactions would be a concerted addition—dehydration mechanism with an oxaphosphirane intermediate (P—C—O membered ring). The presence of phosphonate and allylic protons could explain the ease of dehydration steps observed experimentally to afford the conjugated double bonds.

This one-step addition and dehydration mechanism could be depicted as below. Oxaphosphirane (P—C—O membered ring) is considered as an intermediate, followed by elimination and rearrangement to form the diene. Both the phosphonate and allylic proton facilitate the formation of the conjugated C═C double bonds:

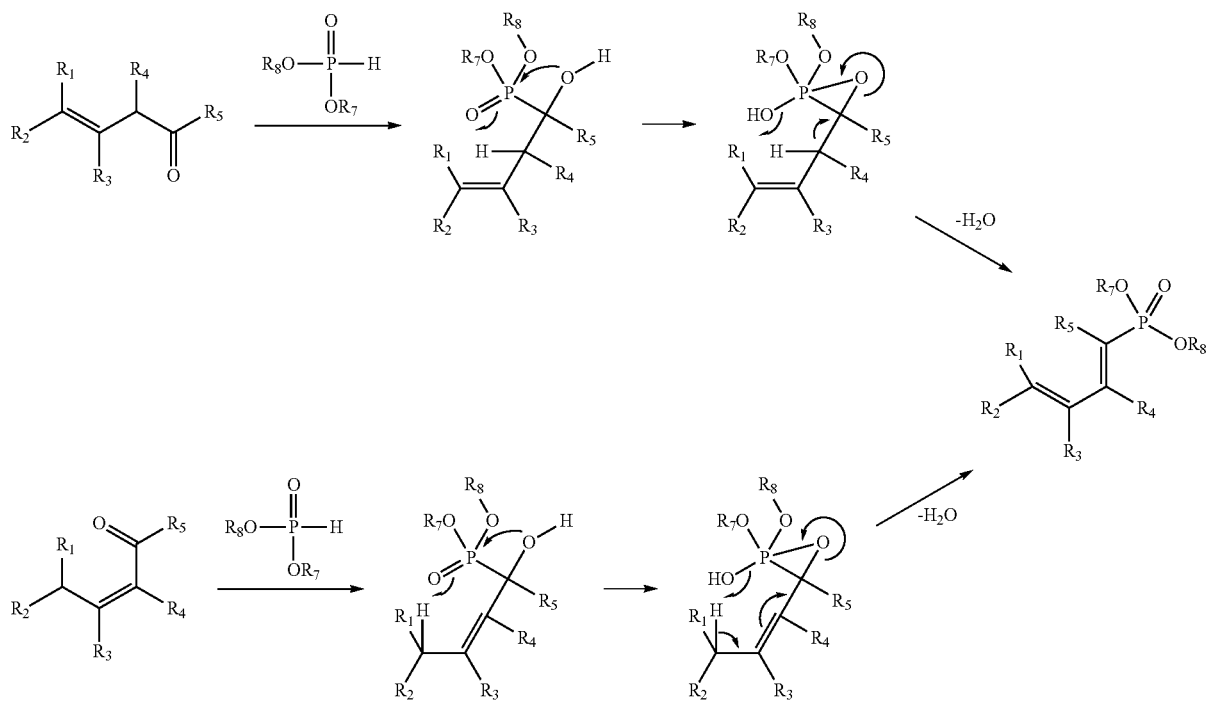

Without wishing to be bound by any existing theory, the preparation method of the present invention is valid whether starting from α,β-unsaturated carbonyl compounds or α,γ-unsaturated carbonyl compounds and both species will lead to the formation of the same diene.

For example, mesityl oxide, was reacted with phosphorous acid in the presence of acetic anhydride and acetic acid under mild conditions to yield 4-methylpenta-2,4-diene-2-phosphonic acid in more than 90% mole purity.

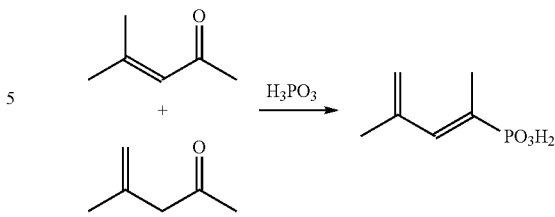

Unlike the reaction described in U.S. Pat. Nos. 7,420,081 and 7,442,831, the formation of the diene monomer involves the rearrangement of the existing double bond if α,β-unsaturated carbonyl compounds are used and the formation of the diene monomer requires much lower reaction temperature in a single step. This behavior has not been described in prior arts even if no C═C rearrangement occurs in the case of β,γ-unsaturated ketones or aldehydes.

When compounds of formula (I) are conjugated diene phosphinate compounds, the method comprises the step of: reacting an α,(- or (,(-unsaturated ketone or aldehyde having the formula II or III,

II

-continued

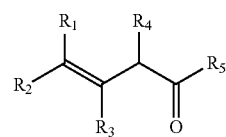

III with a phosphinic acid or its derivatives having the formula,

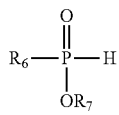

to obtain a conjugated diene phosphinate compound having the formula V,

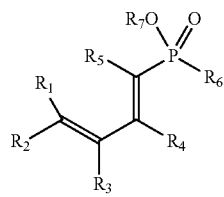

V

The process disclosed in the present invention allows to change the is selectivity of the reaction of phosphinate compounds bearing at least one P—H bond to obtain selectively 1,3-diene compounds when starting from α,β or β,γ-unsaturated carbonyl compounds.

One potential mechanism to explain the selectivity of the reactions would be a concerted addition—dehydration mechanism with an oxaphosphirane intermediate (P—C—O membered ring). The presence of phosphinate and allylic protons could explain the ease of dehydration steps observed experimentally to afford the conjugated double bonds.

This one-step addition and dehydration mechanism could be depicted as below. Oxaphosphirane (P—C—O membered ring) is considered as an intermediate, followed by elimination and rearrangement to form the diene. Both the phosphinate and allylic proton facilitate the formation of the conjugated C=C double bonds:

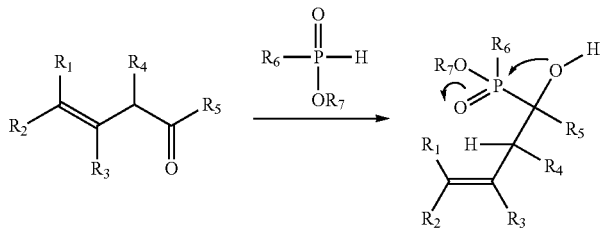

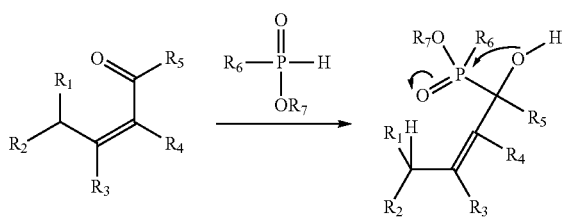

Without wishing to be bound by any existing theory, the preparation method of the present invention is valid whether starting from α,β-unsaturated carbonyl compounds or β,γ-unsaturated carbonyl compounds and both species will lead to the formation of the same diene.

According to an embodiment, said compound II or III is added in the molar ratio of (0.5~2):1 relative to said phosphinic acid or its derivatives; or preferably (1~1.5):1 relative to said phosphinic acid or its derivatives. Usually, the reaction is carried out in organic solvents such as solvent(s) selected from one or more of the group consisting of toluene, cyclohexane, butyl ether. The reaction time remains 4~24 hours, or preferably 4-8 hours. The reaction temperature remains 0~150° C., or preferably 85~125° C.

For example, mesityl oxide, is reacted with hypophosphorous acid in its concentrated form to afford 4-methylpenta-2,4-diene-2-phosphinic acid. The same reaction could be carried out using 50% hypophosphorous acid using toluene as azeotropic solvent to remove water during the reaction. The target monomer can be easily isolated and purified by simple extractions and washes to obtain up to 97% pure product.

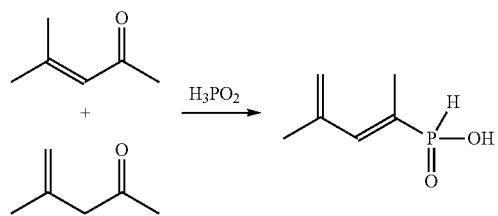

The process described above allows forming a mixture of phosphinate and phosphonate compounds that can be directly polymerized to obtain polymers containing both phosphinate and phosphonate groups in which both functionalities are well known to provide some useful properties such as flame retardant property.

The unsaturated ketones and aldehydes can be obtained from aldol condensations of carbonyl compounds.

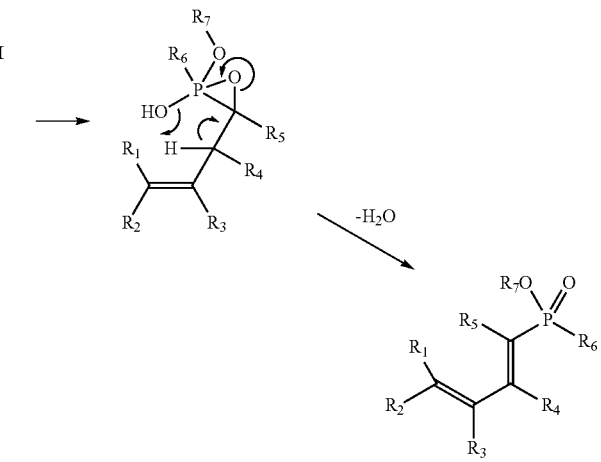

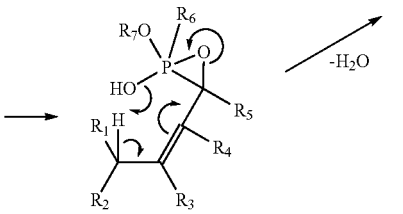

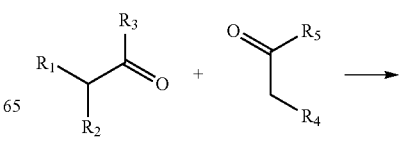

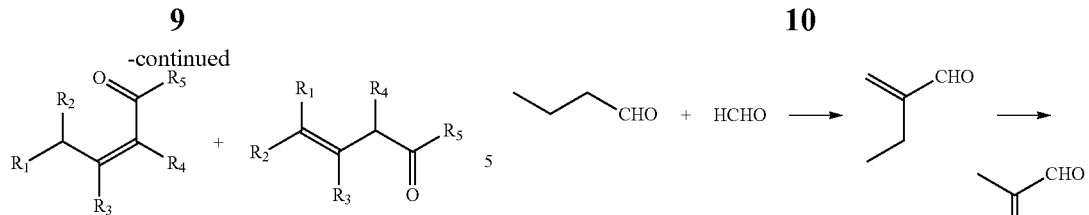

For example, dimerization of methyl isobutyl ketone (MIBK) as taught by U.S. Pat. No. 4,170,609.

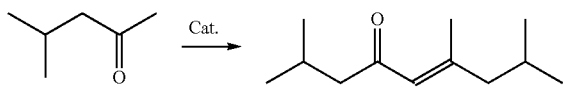

In a similar manner, aldol condensation of pinacolone will yield a highly branched unsaturated ketone:

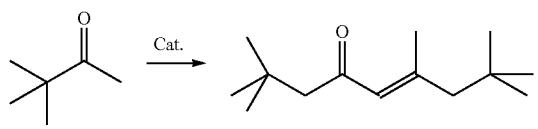

For both methods described above, some commercially available unsaturated ketones and aldehydes may also be used in the present invention. They are important industrial chemicals. They are used as solvents, for example, mesityl oxide, as precursor to other commodity and specialty chemicals, for example, isophorone and as monomer for polymeric materials, for example, methyl vinyl ketone (MVK).

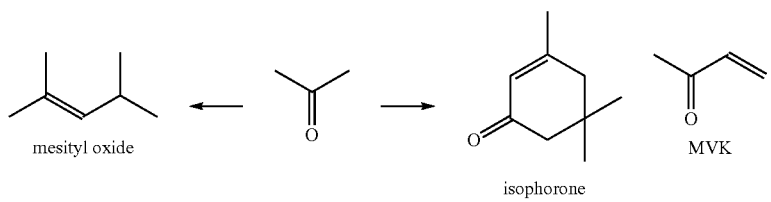

3-Methylcrotonaldehyde is a precursor for Vitamine A. Industrially, it is produced from isobutene and formaldehyde:

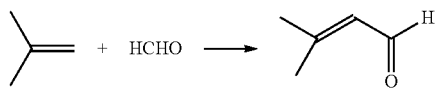

An attractive one may be crotonaldehyde. It is a biogenic compound, used for florvoring. It can be produced from renewable resources of bioethanol:

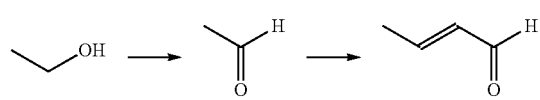

2-Ethyl acrolein, and its isomer of tiglic aldehydes are intermediate for flavor agents (U.S. Pat. No. 4,605,779):

Natural unsaturated ketones and aldehydes can also be used to carry out the reaction. Those include, for example, piperitone, carvone, umbellulone, menthene-2-one, menthene-3-one, verbenone and myrtenal. The resulting phosphonate dienes could be of important biological activities, thus as insecticides, pesticides, pharmaceuticals and their intermediates.

The reaction may be optionally carried out under protection of inert gas protection. Said inert gas may be selected from, for example, one or more of the group consisting of nitrogen, argon, and carbon dioxide.

In step (a), the compounds (I) may advantageously be used as a coating composition comprising said compounds in a solvent. In that case, the solvent is preferably chosen among aqueous and organic solvents. Typically, the molarity of compound of formula (I) in the coating composition may be of between 0.001M and 3M. The obtention of SAMs in step (a) is generally favoured when molarity of compound of formula (I) in the coating composition is less than 2M and more preferably less than 0.5M. Generally, so as to obtain a sufficient coating, it is however preferable that the molarity of compound of formula (I) in the coating composition is of at least 0.005M, more preferably of at least 0.01M.

According to another embodiment, the organic solvent of the coating composition used in step (a) is chosen among alcohols, ketones, alkanes and their mixtures. In a preferred embodiment, the organic solvent of the coating composition used in step (a) is acetone.

According to another possible embodiment, the coating composition is an aqueous composition wherein the solvent is water, said composition being preferably free of any organic solvent. The pH of the aqueous composition may be adjusted between 2 and 14 with organic or inorganic acids or bases.

The coating composition of the present invention can be in the form of a solution, a suspension, an emulsion, a foam or an aerosol. In a preferred embodiment, the coating composition is a solution.

The coating composition can be prepared by using standard blending techniques and equipments for the preparation of homogenous mixtures, suspensions or solutions.

The contacting of the coating composition and the surface of the substrate in step (a) of the present invention can be carried out by any method known per se, especially by dipping, spin-coating, wiping, vaporization, aerosol, spray or printing.

In a preferred embodiment, the contacting is carried out by dipping. In a most preferred embodiment, time of dipping is between 5 seconds and 5 hours, more preferably between 10 seconds and 30 min.

In step (b), the modified surface is submitted to heat or UV, eventually in the presence of radicals, in order to form at least one layer on the surface of the substrate.

In an embodiment, step (b) makes use of a submission to heat which is carried out at a temperature between 20° C. and 150° C., preferably between 80° C. and 150° C., and more preferably between 110° C. and 150° C. during a time between 1 and 30 hours.

In a preferred embodiment, step (b) is carried out under inert atmosphere or under vacuum.

In another embodiment, the submission to UV is carried out during a time between 2 minutes and 2 hours.

In another embodiment, the radicals are chosen among well-known radical initiators or promoter such as azo-bis (isobutyronitrile) (AIBN), di(tert-butyl peroxide), tert-butyl hydroperoxide, benzoylperoxide, or well-known photoinitiators such as nitrogen dioxide, molecular oxygen or 2,2-dimethoxy-2-phenylacetophenone (DMPA).

In some cases, a preliminary treatment of the substrate is carried out before step (a). This preliminary treatment is carried out in order to remove organic and/or inorganic impurities from the surface of the substrate.

In an embodiment of the present invention, the preliminary treatment is an oxidation of the surface of the substrate.

In a preferred embodiment, oxidation is carried out by immersion of the substrate in a boiling "piranha" solution comprising hydrogen peroxide and sulfuric acid or in a nitric acid bath.

After the polymerization of the coating composition in step (b) of the invention, the substrate can be washed in order to improve the anti-wetting properties and/or hydrophobicity of its surface while removing excess coating that is not well organized on the surface.

In an embodiment, washing is carried out with acetone or usual basic washing.

Before or after the step (b) of the invention, the layer can also be modified according to the needs of the desired application.

In an embodiment of the present invention, the modification is carried out by modifying dienes functions in compound of formula (I).

In a preferred embodiment, the modification is carried out by attaching at least one organic group on dienes functions.

In a most preferred embodiment, the organic groups are chosen among thiols, amines, alcohols, or monomeric groups. Acrylates or acrylamides are cited as examples of monomers.

The substrate in the present invention can be chosen among all metallic or inorganic substrates.

In a embodiment, the substrate comprises or consists of titanium, vanadium, chromium, manganese, iron, cobalt, nickel, copper, zinc, aluminum, tungsten, zirconium, steel, stainless steel, or their alloys or oxides such as sapphire or ruby, silicon or germanium, optionally doped, or their oxides or quartz, mica, glass and limestone.

According to a preferred embodiment, the substrate is made of aluminum or its alloys or oxides.

According to another preferred embodiment, the substrate is steel.

According to another preferred embodiment, the substrate is glass or tin oxide.

The method according to the present invention may be used to protect the surface of the substrate against corrosion, to modify its wetting properties and/or hydrophobicity and/or to improve its paintability.

The modification of glass surfaces wettability is also a very wide application with, for example, hydrophobic glass surfaces for building or the surface treatment of glass fibers for improved dispersion in resins or plastics.

EXAMPLES

The present invention is illustrated in greater detail by the examples described herein below.

Example 1

Preparation of 4-methyl-2,4-pentadiene-2-phosphinic acid (PiDM)

In a 100 ml flask were added 16.5 g of hypophosphorous acid ($H_3PO_2$, 50% in to water), 12.25 g of mesityl oxide (a mixture of 1,2- and 1,3-unsaturated ketone) and 20 ml toluene. The mixture was heated under nitrogen to reflux at 125° C. overnight (around 17 hrs), the water was collected and separated out. $^{31}P$ NMR showed 86.4% $H_3PO_2$ was reacted and 4-methyl-2,4-pentadiene-2-phosphinic acid (PiDM) was obtained at 65.4% is selectivity along with other minor impurities.

Example 2

Preparation of 4-methyl-2,4-pentadiene-2-phosphonic acid (PoDM)

Phosphorous acid, $H_3PO_3$ 200 g, which was dried for about 4 hrs at 50° C. under vacuum, and 194 g of acetic acid were added to a 2 L flask with cooling. Then 494 g of acetic anhydride was charged and the temperature rose to 25° C. to yield a colorless homogenous mixture. 1 g of phenothiazine was added and the reaction mixture became light orange. Mesityl oxide (a mixture of 1,2 and 1,3 isomers) 284 g was added drop-wise with stirring over about 4 hrs and the temperature was kept at 23-25° C. The color of the reaction mixture became dark orange after the unsaturated ketone addition. The mixture was then heated to 48° C. for 7 hrs. The product, 4-methyl-2,4-pentadiene-2-phosphonic acid (PoDM) and its anhydride derivative were observed in more than 90% selectivity with 100% conversion of phosphorous acid.

Example 3

Preparation of Glass Coupons Coated with a Layer Obtained from PiDM or PoDM

The glass coupons used were first treated sequentially by immersion in a boiling "piranha" solution (3:1, $H_2O_2$ 30%, $H_2SO_4$ 98%) for 45 minutes to functionalize glass surface by oxidation, rinsing with distillated water. Si samples thus hydrophilic with this treatment were dried in a stream of N2 and immediately used.

Then, the glass coupons treated as described above were held vertically in a solution of PiDM or in a solution of PoDM ($10^{-3}$M in acetone) in a beaker over 3 h. The treated samples were then removed with precaution and heated under vacuum at 150° C. over 20 h to bond the phosphonic acids function to Si02/Si by dehydration. Any multilayer coated during the process was removed by sonication in acetone over 15 minutes. Samples were then dried in hot oven.

Example 4

Evaluation of Anti-Wetting/Hydrophobicity of Glass Coupons Coated with a Layer Obtained from PiDM or PoDM The contact angle of the glass coupons of example 3 was measured. The results are shown in table 1 and FIG. 1.

TABLE 1

|  | Contact angle measurement (°) Without wash |
| --- | --- |
| Benchmark (without treatment) | 31 |
| Benchmark after piranha | 18 |
| PiDM treatment | 53 |
| PoDM treatment | 53 |

Coating by both PiDM and PoDM show an increase in contact angle compared to non coated surface. The treatment allows a modification of the surface, increasing its hydrophobicity/anti wetting properties.

Figure 2:
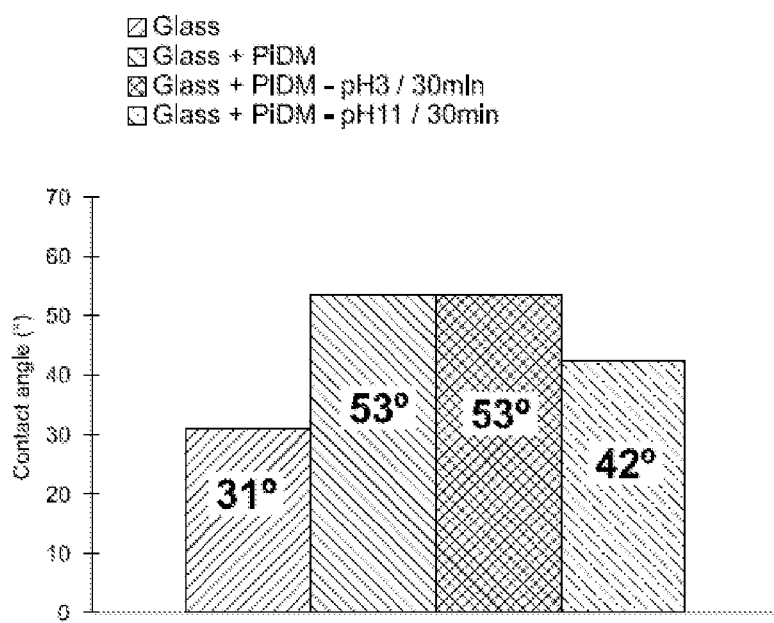
FIG. 2 shows the resistance of the coating of the coupons submitted to treatments in acidic and basic PiDM medium (pH 3 or pH 11 during 30 min).
Figure 3:
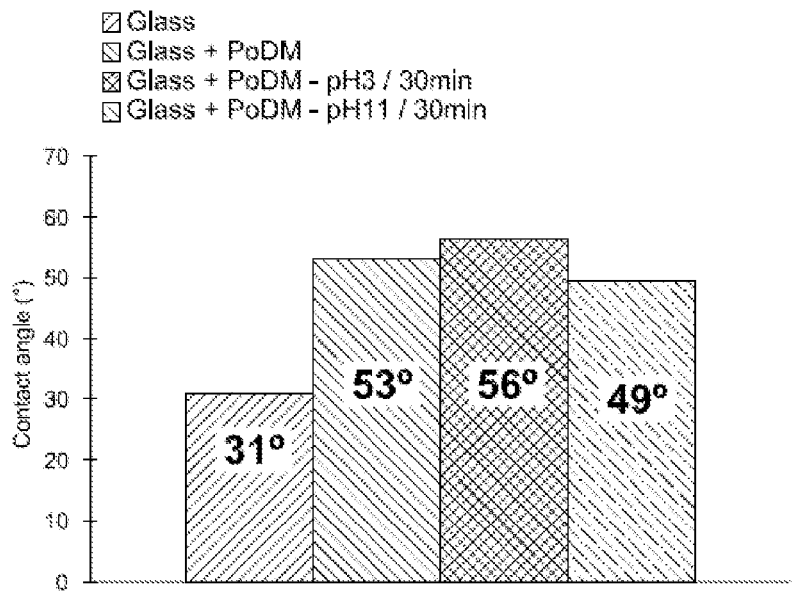
FIG. 3 shows the resistance of the coating of the coupons submitted to treatments in acidic and basic PODM medium (pH 3 or pH 11 during 30 min).

To check the resistance of the coating, coupons are submitted to treatments in acidic and basic medium (pH 3 or pH 11 during 30 min). The results are shown in table 2 and in FIGS. 2 and 3.

TABLE 2

|  | Contact angle measurement (°) | | |
| --- | --- | --- | --- |
|  | Without wash | After acid treatment | After basic treatment |
| Glass (without coating) | 31° | — | — |
| Glass + PiDM | 53° | 53° | 42° |
| Glass + PoDM | 53° | 56 | 49° |

For both coatings, acid treatment shows no significant modification of the contact angle, i.e. no modification of the coating.

For both coatings, basic treatment only shows a slight decrease of the contact angle, i.e. a slight modification of the coating.

Example 5

Figure 4:
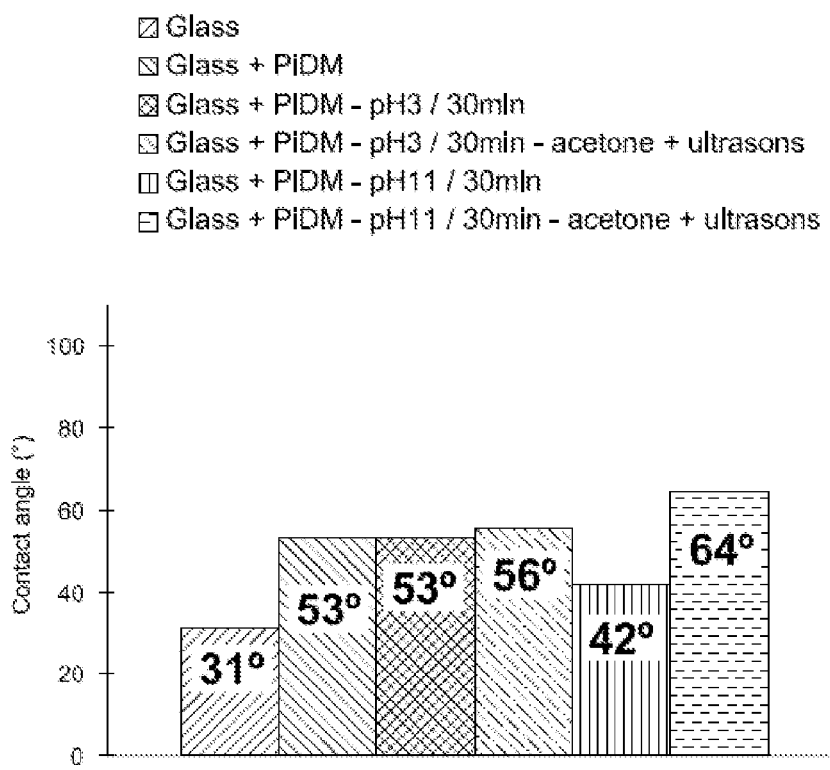
FIG. 4 shows the results of the evaluation of washing with acetone and exposed to ultrasonic on hydrophobicity of glass coupons coated with a layer obtained from PiDM.
Figure 5:
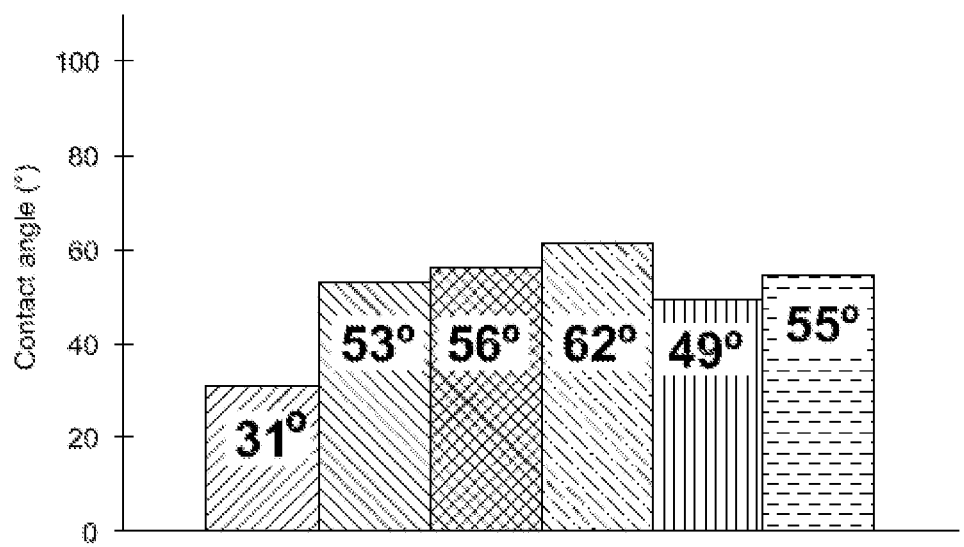
FIG. 5 shows the results of the evaluation of washing with acetone and exposed to ultrasonic on hydrophobicity of glass coupons coated with a layer obtained from PoDM.

Evaluation of Washing with Acetone on Hydrophobicity of Glass Coupons Coated with a Layer Obtained from PiDM or PoDM Coupons of example 4 are washed with acetone and exposed to ultrasonic. The results are shown in table 3 and in FIGS. 4 and 5.

TABLE 3

|  | Contact angle measurement (°) | | | | |
| --- | --- | --- | --- | --- | --- |
|  | Without wash | After acid treatment (pH 3) | After acid treatment (pH3) + Acetone treatment + ultrasonic | After basic treatment (pH 11) | After basic treatment (pH 11) + Acetone treatment + ultrasonic |
| Benchmark (without coating) | 31° | — | — | — | — |
| Benchmark after piranha | 18° | — | — | — | — |
| PiDM | 53° | 53° | 56° | 42° | 64° |
| PoDM | 53° | 56° | 62° | 49° | 55° |

Wash in acetone of treated coupons (acidic or basic medium) shows an increase of hydrophobicity for both PoDM and PiDM.

Example 6

Evaluation of Immersion Time and Molarity of PoDM of the Treatment Solution on Hydrophobicity of Glass Coupons Treated with a Layer Obtained from PoDM Glass coupons coated with a layer obtained from PoDM are prepared as in example 4, with a variable immersion time of glass in the solution of PoDM (0.5, 1, 2 or 3 hours) and a variable molarity of PoDM in the solution (0.05M and 0.25M).

Results are shown in table 4.

TABLE 4

|  |  | Contact angle measurement (°) | | |
| --- | --- | --- | --- | --- |
|  | Immersion time (h) | Without wash | After basic treatment | After basic treatment + Acetone treatment |
| Benchmark (without coating) |  | 31° | — | — |
| PoDM 0.05M | 0.5 | 65° | — | — |
|  | 1 | 68° | 90° | — |
|  | 2 | 66° | 88° | 91° |
|  | 3 | 67° | 96° | 91° |
| PoDM 0.25M | 0.5 | 68° | — | — |
|  | 1 | 68° | 95° | — |
|  | 3 | 66° | 92° | 93° |

A method of coating with a solution of PoDM allows significantly improving the hydrophobicity of treated glass surface, even with a short immersion time.

An increase of the content of PoDM in the treatment solution does not improve the hydrophobicity of treated glass surface.

Example 7

Evaluation of Resistance to Corrosion of Aluminum Coupons Coated with a Layer Obtained from PiDM or PoDM The aluminum coupons used were first treated sequentially by immersion in a nitric acid bath (pH=3), for 1 min at ambient temperature. After rinse with deionized water for 1 min and dry in a stream of N2, the coupons were immediately used.

The treated aluminium coupons were then held vertically in a solution of PiDM or in a solution of PoDM ($10^{-3}$M in acetone) in a beaker over 3 h. The treated samples were then removed with precaution and heated under vacuum at 150° C. over 20 h to bond the phosphonic acids function to Al2O3/Al by dehydration.

Figure 6:
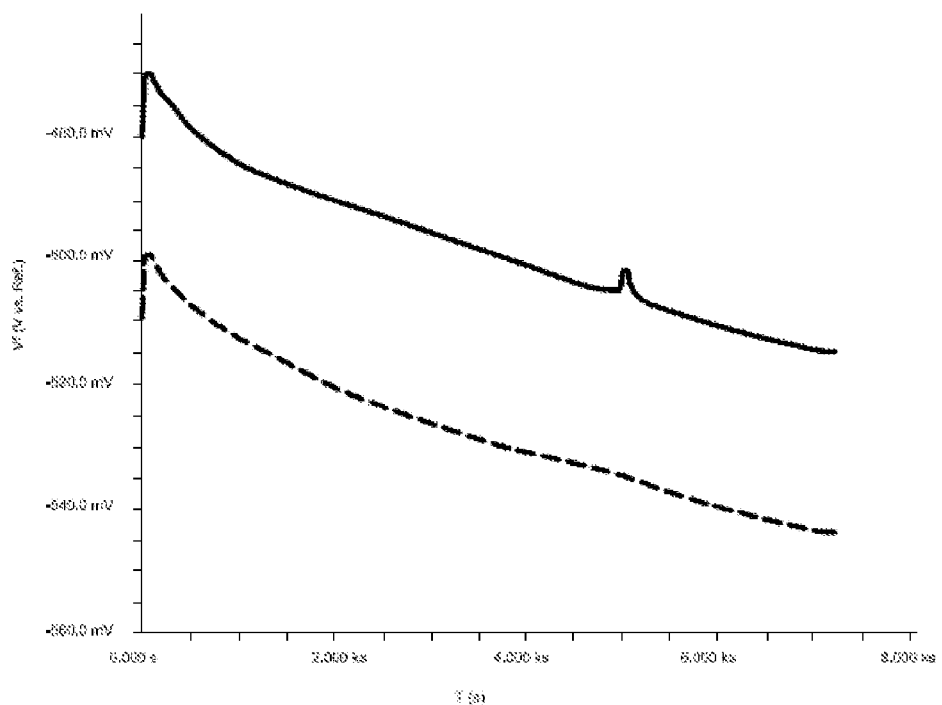
FIG. 6 shows open potential curves (versus ECS) obtained on coated (unbroken line) and naked (discontinuous line) in acidic atmosphere (pH=3).

PoDM and PiDM coatings lead to a modification of the interface between the material and its environment. In several media (acidic, basic), the free potential of PiDM and PoDM coated materials is increased compared to a blank. Open potential curves (versus ECS) obtained on coated (unbroken line) and naked (discontinuous line) in acidic atmosphere (pH=3) are showed in FIG. 6.

Figure 7:
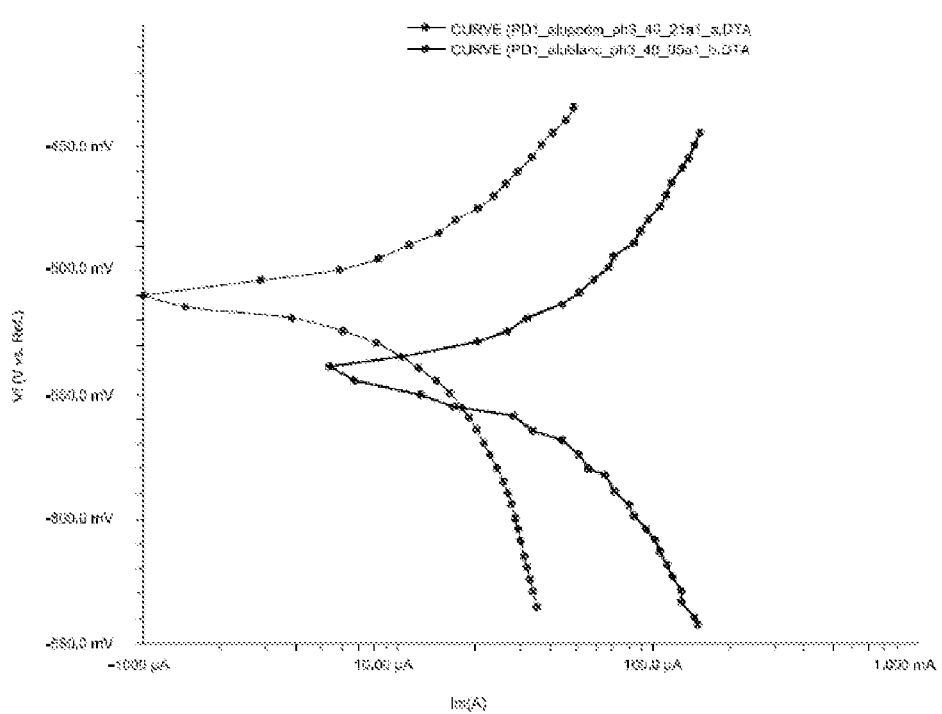
FIG. 7 shows the corrosion rate decreased from 40 μA to 15 μA in acidic environment (pH 3) (thin line).

Simultaneously, the corrosion rate of coated materials is significantly decreased. In acidic environment (pH 3), the corrosion rate is decreased from 40 µA to 15 µA as shown in FIG. 7 (thin line).

Application of PiDM and PoDM on metals leads to a passive layer on the material. In case of naturally passivated materials, the application of PiDM and PoDM reinforces the stability of the natural passive layer.

Homogeneous anticorrosion layer is obtained avoiding also localized corrosion issues even on passivating materials such as aluminum.

The invention claimed is:

1. A method of coating at least one surface of an inorganic substrate with an organic coating, the method comprising the following steps:
   (a) treating the at least one surface of the substrate by contacting said surface with a composition consisting of a solvent and at least one compound having the following formula (I):

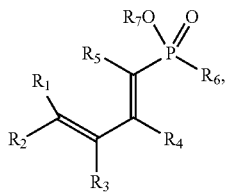

(I)

wherein,
each of $R_1$, $R_2$, $R_3$, $R_4$, and $R_5$, which can be identical or different, and is selected from hydrogen, an alkyl, an aryl, an alkaryl, an aralkyl, a cycloalkyl, a heterocycloalkyl, or an alkenyl group;
$R_6$ is selected from H, an alkyl, an aryl, an alkaryl, an aralkyl, a cycloalkyl, a heterocycloalkyl, an alkenyl group, or an —$OR_8$ group, wherein $R_8$ is selected from a hydrogen, an alkyl, an aryl, an alkaryl, an aralkyl, a cycloalkyl, a heterocycloalkyl, an alkenyl group, or a metal selected from the group consisting of Na, Li, and Ca, or an ammonium compound;
$R_7$ is selected from a hydrogen, an alkyl, an aryl, an alkaryl, an aralkyl, a cycloalkyl, or an alkenyl group, or a metal selected from the group consisting of Na, Li, and Ca, or an ammonium compound;
whereby the at least one compound of formula (I) adsorbs on said surface; and
   (b) submitting the surface of the substrate modified in the treatment of step (a) to heat or UV irradiation;
whereby the at least one compound of formula (I) reacts and forms a stable coating on said surface.

2. The method as defined by claim 1, wherein $R_1$, $R_2$ and $R_4$ are hydrogen; $R_3$ and $R_5$ are methyl; and $R_7$ is hydrogen.

3. The method as defined by claim 1, wherein $R_6$ is hydrogen.

4. The method as defined by claim 1, wherein $R_8$ is hydrogen.

5. The method as defined by claim 1, wherein the compound of formula (I) is a conjugated diene phosphinate.

6. The method as defined by claim 1, wherein the compound of formula (I) is a conjugated diene phosphonate compound having the following formula:

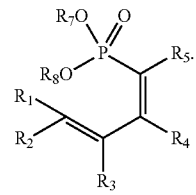

7. The method as defined by claim 1, wherein the method further comprises a preliminary treatment of the substrate before step (a).

8. The method as defined by claim 7, wherein the preliminary treatment comprises oxidation of the surface of the substrate.

9. The method as defined by claim 1, wherein the method further comprises washing of the substrate after step (b).

10. The method as defined by claim 9, wherein the substrate is washed with acetone.

11. The method as defined by claim 1, wherein the substrate comprises steel, aluminium, an alloy thereof, or an oxide thereof.

12. The method as defined by claim 1, wherein the substrate is glass or tin oxide.

13. The method as defined by claim 1, wherein the method protects the substrate against corrosion.

14. The method as defined by claim 1, wherein the method modifies wettability and/or hydrophobicity of the substrate.

15. The method as defined by claim 1, wherein the method improves paintability of the substrate.

* * * * *